US00PP19474P3

(12) United States Plant Patent
Morrow

(10) Patent No.: US PP19,474 P3
(45) Date of Patent: Nov. 25, 2008

(54) ***CYNODON DACTYLON* PLANT NAMED 'OZ-E-GREEN'**

(50) Latin Name: *Cynodon dactylon*
Varietal Denomination: Oz-E-Green

(76) Inventor: Robert William Morrow, Berries Road, Childers, Queensland (AU), 4660

( * ) Notice: Subject to any disclaimer, the term of this patent is extended or adjusted under 35 U.S.C. 154(b) by 0 days.

(21) Appl. No.: 11/507,193

(22) Filed: Aug. 21, 2006

(65) Prior Publication Data

US 2008/0184440 P1 Jul. 31, 2008

(51) Int. Cl.
*A01H 5/00* (2006.01)

(52) U.S. Cl. ..... Plt./389
(58) Field of Classification Search ..... Plt./389
See application file for complete search history.

(56) References Cited

U.S. PATENT DOCUMENTS

PP11,181 P 1/2000 Riley
PP13,059 P2 10/2002 Brown

OTHER PUBLICATIONS

UPOV–ROM–GTITM Plant Variety Database Feb. 2007, GTI Jouve Retrieval Software, Citation for Cynodon 'Oz–E–Green', one page.*
Oz Tuff Turf [online], [retrieved on Sep. 20, 2007]. Retrieved from the Internet <http://www.ozluffturf.com.au/home.php> 3 pages.*
RJ & ML Riley Ltd, Riley's Super Sport, Plant Varieties Journal, 1995, vol. 9, No. 2.
Triodia Pty Ltd, Plateau, Plant Varieties Journal, 2003, vol. 12, No. 2.
Tropical Lawn Pty Ltd, TL1, Plant Varities Journal, 2003, vol. 16, No. 4.
Oz Tuff Turf, Oz–E–Green, Plant Varities Journal 2004, vol. 17, No. 1.

* cited by examiner

*Primary Examiner*—Kent L. Bell
*Assistant Examiner*—June Hwu
(74) *Attorney, Agent, or Firm*—Ostrager Chong Flaherty & Broitman P.C.; Manette Dennis

(57) ABSTRACT

An asexually reproduced new variety of *Cynodon dactylon* with a unique combination of morphological characters including superior turf performance characterized by dense prostrate habit, slow rate of lateral spread, short internode length, low numbers of inflorescences and inflorescence spikes, and a dark green colour.

1 Drawing Sheet

FIELD OF INVENTION

The present invention relates to a new and distinct variety of *Cynodon dactylon* (L.) Pers plant, botanically known as *Cynodon dactylon,* and hereinafter referred to by the variety name 'Oz-E-Green'.

*Cynodon dactylon* is a member of the grass family and has common names of Bermudagrass in the United States and green couch grass in Australia. It is typical for this species to be used for turf. 'Oz-E-Green' has demonstrated high turf quality and is useful for golf course fairways, tees, residential and commercial lawns, sports fields, recreational areas, such as parks, and other similar applications.

BACKGROUND OF THE INVENTION

The new 'Oz-E-Green' is a unique chance seedling or a spontaneous mutant discovered by the Inventor in 2001 in the fringes of a cultivated turf area of 'Queensland' blue couch (*Digitaria didactyla*) near Childers, Queensland, Australia. The fringe area included 'Common' green couch (*Cynodon dactylon*), but the new variety stood out as being very different from the surrounding green couch and the cultivated blue couch. Having demonstrated superior turf characteristics, a selected piece of sod was removed, broken into vegetative sprigs and propagated. Asexual reproduction of the new variety by vegetative sprigs since 2001, in the nursery area of the turf farm where it was discovered near Childers, Queensland, Australia, has shown that the unique features of this new *Cynodon dactylon* variety are stable and reproduced true to type in six successive generations.

As 'Oz-E-Green' is very short in vertical growth height, even when not mown for an extended period, 'Plateau', 'TL1' and 'Riley's Super Sport' were identified as being lower growing varieties than other *Cynodon dactylon* cultivars and may be considered to be the most similar varieties.

'Plateau' is disclosed in U.S. Plant Pat. No. 13,059 and Australian PBR No. 1439. 'Riley's Super Sport' is disclosed in U.S. Plant Pat. No. 11,181 and Australian PBR No. 739 and 'TL1' is disclosed in Australian PBR No. 2638.

SUMMARY OF THE INVENTION

Plants of the variety 'Oz-E-Green' have not been observed under all possible environmental conditions. The phenotype may vary somewhat with variations in environment such as temperature, light intensity and day length without, however, any variance in genotype.

The following traits have been repeatedly observed and are determined to be the unique characteristics of 'Oz-E-Green'. These characteristics in combination distinguish 'Oz-E-Green' as a new and distinct cultivar:

1. very prostrate growth habit (i.e. having a very short vertical growth height),
2. fine leaf texture,
3. short internode length, 4. slow lateral extension growth rate,
5. forms a dense mat,
6. low numbers of inflorescences,
7. low number of spikes per inflorescence,
8. short spike length, and
9. dark green colour (RHS N138B).

Other significantly different features demonstrated from the comparative growing trial are described herein. Advantageously these properties may directly relate to the selection criteria of the new variety of 'Oz-E-Green', which was based on dense prostrate habit, limited inflorescence production (contributing to a low mowing requirement), high turf quality, and attractive dark green colour.

The new variety is propagated vegetatively (asexual reproduction) by sod, plugs, sprigs, tillers, rhizomes or stolons. Vegetative propagation has established that the characteristics have been passed through six generations without showing any discernible off types.

The putative parent 'Common' green couch (or common Bermudagrass as it is known in the United States) was observed in the region of the discovery site of the new variety near Childers, Queensland, Australia, where it was in the vicinity of 'Oz-E-Green' growing in the fringe of a cultivated turf growing area of 'Queensland' blue couch. 'Common' green couch was considered to be so different to 'Oz-E-Green' that it was not considered to be pertinent at all to comparative trials by the inventor and the qualified person who conducted the trials.

'Common' green couch has coarser textured leaves and stems, more open and erect growth (does not form a dense mat in comparison to the new variety), profuse inflorescence production, more spikes per inflorescence, longer inflorescence spikes, and a lighter green leaf colouring. It also spreads laterally more rapidly than the 'Oz-E-Green'.

DETAILED BOTANICAL DESCRIPTION

Figure 1:
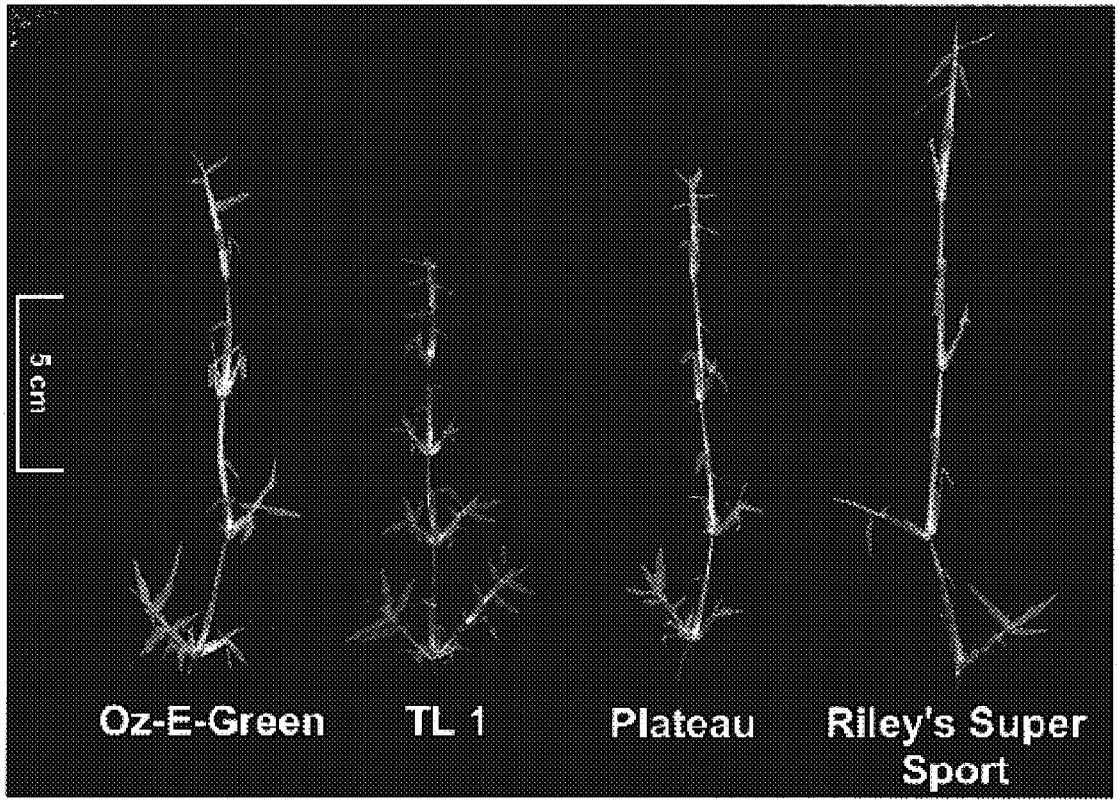
FIG. 1 shows a comparison of the new variety 'Oz-E-Green' to 'Plateau', 'TL1' and 'Riley's Super Sport'.
Figure 2:
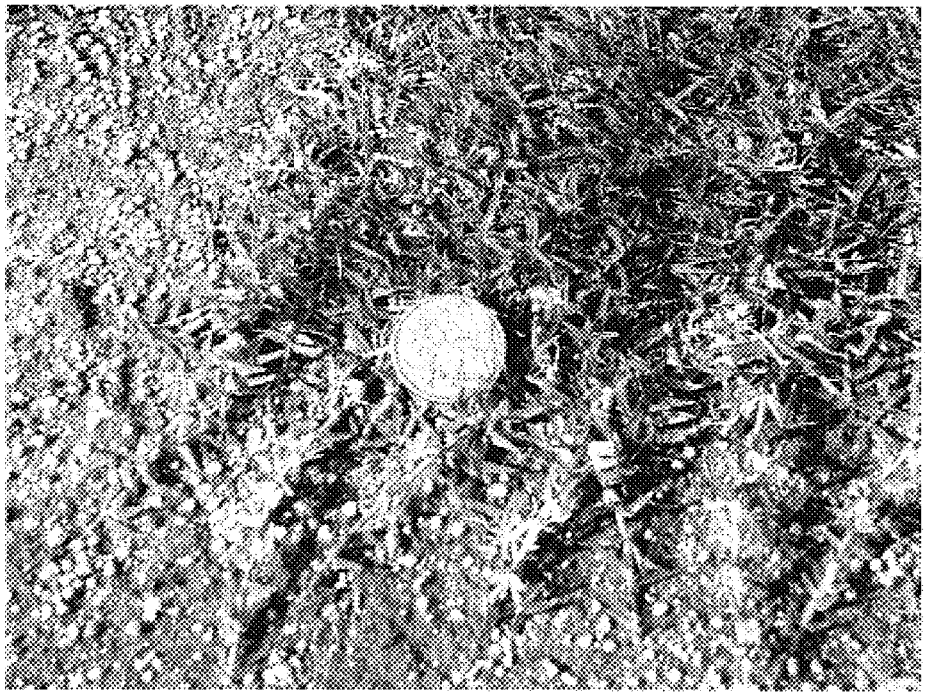
FIG. 2 shows the turf appearance of the new variety.

Latin name of the genus and species of the plant claimed: The present invention relates to the genus and species *Cynodon dactylon* (L.) Pers.

Variety denomination: 'Oz-E-Green'.

Plants of the variety 'Oz-E-Green' have not been observed under all possible environmental conditions. The phenotype may vary somewhat with variations in environment such as temperature, light intensity and day length without, however, any variance in genotype.

1. Origin and Breeding

'Oz-E-Green' is a new variety of *Cynodon dactylon* which is suitable for use as turf in all areas, and in particular to golf course fairways, tees, residential and commercial lawns, sports fields, playing areas and the like. 'Oz-E-Green' is a spontaneous mutation or a chance seedling discovered in an area where there was 'Common' green couch and located on the fringe of a cultivated turf area of 'Queensland' Blue Couch (*Digitaria didactyla*) near Childers, Queensland, Australia in 2001. Given the location of 'Oz-E-Green', it is assumed 'Common' green couch may be the putative parent. *Cynodon dactylon* is considered to be genetically stable so it more likely 'Oz-E-Green' is a chance seedling. However spontaneous mutation was also considered as an option for the origin of 'Oz-E-Green' due the significantly differing plant characteristics.

The cultivated turf area of 'Queensland' blue couch was unfertilized at the time making it easier to locate contaminant grasses in the turf area and fringes for the purpose of spot spraying for quality assurance. The new variety was discovered in the fringes by the Inventor as being substantially different to other 'Common' green couch grasses displaying the potential characteristics that would be advantageous for turf performance. 'Oz-E-Green' was then marked for further observation.

Having been observed for a short period, 'Oz-E-Green' demonstrated superior turf characteristics and a selected piece of sod was removed. It was broken apart and washed to ensure there were no impurities and vegetative sprigs were removed to propagate a larger area of this variety elsewhere on the breeder's property. The original selected plant has been vegetatively propagated in six successive generations without showing any discernible off types and has remained true to type demonstrating distinctiveness, uniformity and stability. The selection criteria for 'Oz-E-Green' were that it had a dense prostrate habit, limited inflorescence production (giving a low mowing requirement), high turf quality, and dark green colour.

2. Characteristics

The description of the variety is taken from comparative trials conducted between Aug. 24, 2003 to Mar. 16, 2004 in Cleveland, Queensland, Australia (Latitude 27°32' South, Longitude 153°15' East, elevation 25 masl). The soil type was a ferrosol (Isbell, R.F. (2002) 'The Australian Soil Classification'. Revised Edition. CSIRO Publishing, Collingswood, Victoria, Australia). The characteristics of the new variety are as follows with all R.H.S. Colour Chart numbers referring to 2001 edition.

Classification: *Cynodon dactylon* (L.) Pers. 'Oz-E-Green'.

Parentage: Putative parent is 'Common' green couch as commonly known in Australia or 'Common' Bermudagrass as it is commonly know in the United States.

Propagation: Vegetatively (asexual reproduction) by sod, plugs, sprigs, tillers and pieces of rhizomes or stolons.

Growth habit: Habit creeping, type tight mat-forming, height very short, longevity perennial, spreading laterally by stolons and rhizomes.

Leaf blade: Shape linear-triangular, length medium-short, width medium.

Vegetative leaf: In the comparative trials, the $4^{th}$ youngest visible node was used as the standard for the leaf measurements as it was considered that no further leaf blade expansion is likely and senescence or other forms of destruction or deterioration (such as by insects, disease, etc) is unlikely to have occurred.

*Blade length range.*—Mean tiller 4th leaf blade length is 28.2 mm. (Range 16.4–43.0 mm). Mean stolon 4th leaf blade length is 8.6 mm. (Range 4.2–17.9 mm).

*Blade width mean.*—Mean tiller 4th leaf blade width 2.09 mm. Mean stolon 4th leaf blade width 2.30 mm.

*Sheath length mean.*—Mean tiller 4th leaf sheath length 10.29 mm. Mean stolon 4th leaf sheath length 7.7 mm.

Stolon: Compound nodes with up to 3 leaves, internode length short, internode thickness medium, colour grey-brown (RHS N199B) when exposed to sunlight.

Ligule: Dense row of short white hairs.

Inflorescence: Digitate with (3-)4 short spicate racemes.

*Culm.*—Length very short.

*Peduncle.*—Length very short — mean length 65.6 mm and mean diameter 0.51 mm.

*Spike length.*—Mean length 25.2 mm.

*Flag leaf blade length.*—Mean length 16.1 mm.

*Flag leaf blade width.*—Mean width 1.79 mm.

Color notations:

*Leaf blade color adaxial leaf surface.*—Dark green RHS N138B (summer).

*Stolon color.*—RHS N199B (summer, exposed to sunlight).

Disease susceptibility: From observations of Oz-E-Green in a cultivated environment, it was noted the new variety is not as prone to fungus, bacteria and rot to the plant stems or stolons from thatch or clippings that falls on top of the turf in comparison to 'Common' green couch.

3. Comparative Trials

The grouping characteristics used in identifying the most similar varieties of common knowledge was creeping habit, mat-forming type and very short height. 'Plateau'[A], 'TL1'[A] and 'Riley's Super Sport'[A] are lower growing than other *Cynodon dactylon* cultivars and therefore considered to the most similar varieties. This selection was based on their growth in a world collection of 138 turf grasses and general knowledge of the persons conducting the trial.

The putative parent 'Common' green couch was excluded because it is readily distinguishable from 'Oz-E-Green' by its coarser, more open and erect growth, and lighter green leaves.

On Aug. 24, 2003, 5 cm cores were planted spaced apart 1 m×1 m. The plants were not defoliated and weed control was by pre-emergence oxidation. Nutrition was maintained with slow release fertilisers. The experimental design of the trial involved 30 plants per variety with 5 plants per plot in 6 randomised blocks. Two measurements were taken per plant. The diameter of spread measurements was take on Nov. 21, 2003, stolon leaf and internode measurements were taken on Dec. 17–18, 2003, shoot and inflorescence measurements were taken on Dec. 18, 2003–Jan. 12, 2004 and leaf and stolon colour on Mar. 16, 2004 on the spaced plants. The results of the comparative trials are shown in Table 1 below calculated to a significance of 1%. FIG. 1 illustrates distinctive features of the new variety.

Referring to Table 1, it is evident from the substantial variation in the measurements that TL1 has significantly different morphological characteristics than 'Oz-E-Green', 'Plateau' and 'Riley's Super Sport' despite being low growing. For example, when compared to the three varieties 'TL1' is the slowest growing grass as indicated by the mean diameter of spread on the spaced plants. It also has the shortest internodes and the shortest stolon leaf blade length, but the longest leaf blade length indicating that it is more coarse textured than the other cultivars in the trial. These differences are illustrated in FIG. 1 which clearly shows the dissimilar morphology to 'Oz-E-Green'.

Compared to 'Plateau' and 'Riley's Super Sport', 'Oz-E-Green' is slower to spread laterally as shown by the mean plant diameter of the spaced plants after 89 days. Similarly, the length of the fourth internode on 'Oz-E-Green' was the shortest. Its relatively slow lateral growth and short stolon internodes indicate that 'Oz-E-Green' forms a tight mat. This is especially so compared to 'Riley's Super Sport' which had the longest stolon internodes and was the fastest spreading. Another difference is that the new variety has thinner stolons.

'Oz-E-Green' produced fewer spikes than both of the comparator varieties. This indicates a lower mowing requirement which in particular would be advantageous in large areas of turf that require high maintenance such as a golf course. When produced, the inflorescence spikes of 'Oz-E-Green' are longer than 'Plateau' but shorter than 'Riley's Super Sport' and the peduncle length is significantly longer than the comparators.

The leaf texture of the new variety is fine and similar to the textures of the two comparator varieties. Stolon leaf blades on 'Oz-E-Green' are not significantly different in length to those of 'Plateau' and 'Riley's Super Sport', but are significantly narrower than on 'Plateau' as also shown by the greater length:width ratio. The length of stolon leaf sheaths on 'Oz-E-Green' is also shorter than on the two comparators.

In unmown swards, the flag leaf blades on flowering tillers of 'Oz-E-Green' are significantly longer than on 'Plateau', while the flag leaf blades are significantly and wider than those of 'Plateau' and 'Riley's Super Sport'. The leaf sheaths on flowering tillers of 'Oz-E-Green' are significantly shorter than on 'Riley's Super Sport'.

Other differences are evident from the comparative data presented in Table 1.

The new and distinct variety 'Oz-E-Green' is an excellent quality turf grass variety of *Cynodon dactylon* having distinguishing features from low growing 'Plateau', 'Riley's Super Sport' and 'TL1' and 'Common' Bermudagrass.

The ligule consists of a dense row of short hairs about 0.2 to 0.5 mm long on a membranous rim with longer hairs about 1.0 to 1.5 mm long at each end. The leaf blades are flat or slightly V-shaped, linear-triangular in shape, about 2.5 to 3.5 mm long, about 2.0 mm wide, pointed, glabrous or very sparsely pubescent both on the upper (adaxial) surface and on the lower (abaxial) surface, minutely scabrous on the margin. Auricles are absent. The sheath is glabrous, split with margins overlapping. The collar is a continuous narrow band. Leaves are folded in the bud shoot, with vernation conduplicate.

Culms are decumbent to erect, about 20 to 80 mm long and about 1.0 to 2.0 mm wide. The term "flag leaf" is used to refer to the highest leaf on a flowering culm, immediately below the inflorescence.

The inflorescence is digitate with (3-)4 short spicate racemes about 20–30 mm long, peduncles are short, about 50–80 mm long. The rhachis is flattened, with spikelets packed broadside to rhachis, regular, 2-rowed.

Spikelets are appressed, solitary. Fertile spikelets are at least 3-flowered, comprising 1 fertile floret, without rhachilla extension, ovate, laterally compressed, 1.8–3 mm long, breaking up at maturity. Spikelets disarticulate below each fertile floret.

Glumes are persistent, similar, subequal in width, thinner than the fertile lemma. The lower glume is lanceolate and equal to the upper glume, herbaceous, 1-keeled, 1-nerved. Lateral nerves are absent in both the upper and the lower glumes. The apex on both the upper and the lower glumes is acute. The upper glume is lanceolate, 50–80% of the length of the adjacent fertile lemma, herbaceous, 1-keeled, 1-nerved.

The fertile lemma is ovate, laterally compressed, 1.8–3 mm long, cartilaginous, wingless, 3-nerved. Lemma midnerve pubescent. Lemma apex acute. Palea 2-nerved. Palea keels eciliate. Anthers 1–1.2 mm long. Anthers and stigmas purple. Grain (caryopsis) with adherent pericarp, ellipsoid, laterally compressed.

TABLE 1

| | 'Oz-E-Green' | *'Plateau'[A] | *'TL1' | *'Riley's Super Sport'[A] |
|---|---|---|---|---|
| MEAN PLANT DIAMETER OF SPACED PLANTS AFTER 89 DAYS (cm) | | | | |
| mean | 70.9 | 95.3 | 39.6 | 134.2 |
| std deviation | 29.7 | 26.5 | 11.6 | 37.1 |
| LSD/sig | 24.9 | ns | P ≦ 0.01 | P ≦ 0.01 |
| FIRST STOLON NODE WITH SECOND LATERAL BRANCH (mm) | | | | |
| mean | 0.98 | 0.92 | 1.27 | 0.75 |
| std deviation | 0.29 | 0.38 | 0.48 | 0.44 |
| LSD/sig | 0.163 | ns | P ≦ 0.01 | P ≦ 0.01 |
| LENGTH OF FOURTH INTERNODE FROM STOLON TIP (mm) | | | | |
| mean | 31.7 | 37.6 | 19.4 | 52.1 |
| std deviation | 5.1 | 3.7 | 3.5 | 6.5 |
| LSD/sig | 2.7 | P ≦ 0.01 | P ≦ 0.01 | P ≦ 0.01 |
| DIAMETER OF FOURTH INTERNODE FROM STOLON TIP (mm) | | | | |
| mean | 1.69 | 1.77 | 1.69 | 1.84 |
| std deviation | 0.16 | 0.16 | 0.10 | 0.18 |
| LSD/sig | 0.08 | P ≦ 0.01 | ns | P ≦ 0.01 |
| LENGTH OF LEAF SHEATH ON FOURTH VISIBLE NODE FROM STOLON TIP (mm) | | | | |
| mean | 7.7 | 10.4 | 5.7 | 13.0 |
| std deviation | 1.1 | 1.6 | 0.9 | 1.4 |
| LSD/sig | 0.9 | P ≦ 0.01 | P ≦ 0.01 | P ≦ 0.01 |
| LENGTH OF LEAF BLADE ON FOURTH VISIBLE NODE FROM STOLON TIP (mm) | | | | |
| mean | 8.6 | 7.2 | 6.6 | 9.1 |
| std deviation | 3.0 | 1.5 | 1.6 | 3.0 |
| LSD/sig | 1.9 | ns | P ≦ 0.01 | ns |
| WIDTH OF LEAF BLADE ON FOURTH VISIBLE NODE FROM STOLON TIP (mm) | | | | |
| mean | 2.30 | 2.66 | 3.14 | 2.21 |
| std deviation | 0.31 | 0.27 | 0.33 | 0.36 |
| LSD/sig | 0.22 | P ≦ 0.01 | P ≦ 0.01 | ns |
| LENGTH:WIDTH RATIO OF LEAF BLADE ON FOURTH VISIBLE NODE FROM STOLON TIP | | | | |
| mean | 3.69 | 2.70 | 2.12 | 4.07 |
| std deviation | 0.99 | 0.51 | 0.53 | 1.02 |
| LSD/sig | 0.59 | P ≦ 0.01 | P ≦ 0.01 | ns |
| LENGTH OF SHEATH ON FLAG LEAF ON FLOWERING TILLERS (mm) | | | | |
| mean | 35.6 | 36.1 | 31.4 | 42.6 |
| std deviation | 7.1 | 7.7 | 5.0 | 5.4 |
| LSD/sig | 4.9 | ns | ns | P ≦ 0.01 |
| LENGTH OF BLADE ON FLAG LEAF ON FLOWERING TILLERS (mm) | | | | |
| mean | 16.1 | 8.5 | 5.0 | 14.9 |
| std deviation | 6.7 | 4.4 | 2.6 | 5.4 |
| LSD/sig | 3.1 | P ≦ 0.01 | P ≦ 0.01 | ns |
| WIDTH OF BLADE ON FLAG LEAF ON FLOWERING TILLERS (mm) | | | | |
| mean | 1.79 | 1.40 | 1.20 | 1.50 |
| std deviation | 0.29 | 0.37 | 0.34 | 0.31 |
| LSD/sig | 0.21 | P ≦ 0.01 | P ≦ 0.01 | P ≦ 0.01 |

TABLE 1-continued

| | 'Oz-E-Green' | *'Plateau'[A] | *'TL1' | *'Riley's Super Sport'[A] |
|---|---|---|---|---|
| LENGTH:WIDTH RATIO OF FLAG LEAF BLADE ON FLOWERING TILLERS | | | | |
| mean | 8.84 | 5.82 | 4.06 | 9.89 |
| std deviation | 3.02 | 1.90 | 1.40 | 2.75 |
| LSD/sig | 1.74 | P ≦ 0.01 | P ≦ 0.01 | ns |
| LENGTH OF SHEATH ON FOURTH LEAF ON FLOWERING TILLERS (mm) | | | | |
| mean | 10.29 | 10.18 | 10.40 | 12.47 |
| std deviation | 1.85 | 2.40 | 2.03 | 2.64 |
| LSD/sig | 1.742 | ns | ns | P ≦ 0.01 |
| LENGTH OF BLADE ON FOURTH LEAF ON FLOWERING TILLERS (mm) | | | | |
| mean | 28.2 | 20.7 | 17.7 | 31.1 |
| std deviation | 6.3 | 6.9 | 6.4 | 6.7 |
| LSD/sig | 5.5 | P ≦ 0.01 | P ≦ 0.01 | ns |
| WIDTH OF BLADE ON FOURTH LEAF ON FLOWERING TILLERS (mm) | | | | |
| mean | 2.09 | 2.32 | 2.09 | 2.07 |
| std deviation | 0.28 | 0.34 | 0.36 | 0.21 |
| LSD/sig | 0.249 | ns | ns | ns |
| LENGTH:WIDTH RATIO OF FOURTH LEAF BLADE ON FLOWERING TILLERS | | | | |
| mean | 13.59 | 8.84 | 8.49 | 15.17 |
| std deviation | 3.14 | 2.47 | 2.84 | 3.53 |
| LSD/sig | 2.17 | P ≦ 0.01 | P ≦ 0.01 | ns |
| LENGTH OF PEDUNCLE ON FLOWERING TILLERS (mm) | | | | |
| mean | 65.6 | 41.9 | 36.2 | 51.6 |
| std deviation | 14.4 | 8.7 | 6.9 | 9.8 |
| LSD/sig | 12.3 | P ≦ 0.01 | P ≦ 0.01 | P ≦ 0.01 |
| DIAMETER OF PEDUNCLE ON FLOWERING TILLERS (mm) | | | | |
| mean | 0.51 | 0.52 | 0.51 | 0.53 |
| std deviation | 0.06 | 0.09 | 0.07 | 0.09 |
| LSD/sig | 0.06 | ns | ns | ns |
| AVERAGE LENGTH OF SPIKES (mm) | | | | |
| mean | 25.2 | 26.5 | 21.9 | 33.0 |
| std deviation | 2.9 | 5.4 | 3.1 | 5.2 |
| LSD/sig | 3.3 | ns | P ≦ 0.01 | P ≦ 0.01 |
| NUMBER OF SPIKES PER INFLORESCENCE | | | | |
| mean | 3.60 | 3.90 | 4.08 | 3.95 |
| std deviation | 0.50 | 0.57 | 0.33 | 0.29 |
| LSD/sig | 0.30 | P ≦ 0.01 | P ≦ 0.01 | P ≦ 0.01 |
| MAXIMUM NUMBER OF SPIKES PER INFLORESCENCE | | | | |
| | 4 | 5 | 5 | 5 |
| STOLON COLOUR EXPOSED TO SUNLIGHT (RHS, 2001) | | | | |
| | N199B | N199B | N199A | N199A |
| LEAF COLOUR (RHS, 2001) | | | | |
| | N138B | 147A | 147A | N138B |

What is claimed is:

1. A new and distinct variety of *Cyondon dactylon* plant, substantially as described and illustrated herein, characterized particularly by a unique combination of morphological characters.

* * * * *